(12) United States Patent
Hurst

(10) Patent No.: US 6,565,546 B1
(45) Date of Patent: May 20, 2003

(54) URINE BAG HOLDER

(76) Inventor: Duane V. Hurst, 8554 122nd Ave. NE. PMB #1, Kirkland, WA (US) 98033

( * ) Notice: Subject to any disclaimer, the term of this patent is extended or adjusted under 35 U.S.C. 154(b) by 0 days.

(21) Appl. No.: 09/844,764

(22) Filed: Apr. 27, 2001

(51) Int. Cl.[7] ............................................. A61F 5/44
(52) U.S. Cl. ...................................... 604/353; 604/349
(58) Field of Search ............................ 604/544, 345, 604/353, 327, 349

(56) References Cited

U.S. PATENT DOCUMENTS

| | | | | |
|---|---|---|---|---|
| 3,897,785 A | * | 8/1975 | Barto, Jr. .................... 128/295 |
| 4,073,295 A | | 2/1978 | Laufbahn | |
| 4,421,509 A | * | 12/1983 | Schneider et al. .......... 604/317 |
| 4,511,358 A | * | 4/1985 | Johnson et al. ............. 224/191 |
| 4,846,816 A | * | 7/1989 | Manfredi ..................... 604/323 |
| 5,032,118 A | * | 7/1991 | Mason ......................... 604/349 |
| 5,087,251 A | * | 2/1992 | Heyman et al. ............. 604/327 |
| 5,234,420 A | * | 8/1993 | Horton et al. ............... 224/663 |
| 5,496,300 A | * | 3/1996 | Hirsch et al. ........... 137/614.05 |
| 5,643,236 A | * | 7/1997 | Hadley ................. 128/DIG. 15 |
| D382,055 S | | 8/1997 | Cassidy et al. | |

FOREIGN PATENT DOCUMENTS

GB          2 215 211 A    *   9/1989

* cited by examiner

Primary Examiner—Weilun Lo
Assistant Examiner—Linh Truong

(57) ABSTRACT

A urine bag holder for removably holding a urine bag to a leg of a user. The urine bag holder includes a panel having a top edge, a bottom edge, a first end edge and a second end edge. The panel comprising a flexible material having a inside surface and an outside surface. Each of a plurality of straps is attached to the outside surface and is positioned generally adjacent to the first end edge. Each of a plurality of fastening members removably fastens free ends of each of the straps to the outside surface of the panel. A plurality of securing members removably secure a urine bag to the panel by engaging holes in the urine bag.

1 Claim, 2 Drawing Sheets

URINE BAG HOLDER

BACKGROUND OF THE INVENTION

1. Field of the Invention

The present invention relates to urine bag holding devices and more particularly pertains to a new urine bag holder for removably holding a urine bag to a leg of a user.

2. Description of the Prior Art

The use of urine bag holding devices is known in the prior art. More specifically, urine bag holding devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,511,358; 3,897,785; 4,486,816; 4,073,295; 5,643,236; and U.S. Des. Pat. No. 382,055.

While these devices fulfill their respective, particular objectives and requirements, the aforementioned patents do not disclose a new urine bag holder. The inventive device includes a panel having a top edge, a bottom edge, a first end edge and a second end edge. The panel comprising a flexible material having a inside surface and an outside surface. Each of a plurality of straps is attached to the outside surface and is positioned generally adjacent to the first end edge. Each of a plurality of fastening members removably fastens free ends of each of the straps to the outside surface of the panel. A plurality of securing members removably secure a urine bag to the panel by engaging holes in the urine bag.

In these respects, the urine bag holder according to the present invention substantially departs from the conventional concepts and designs of the prior art, and in so doing provides an apparatus primarily developed for the purpose of removably holding a urine bag to a leg of a user.

SUMMARY OF THE INVENTION

In view of the foregoing disadvantages inherent in the known types of urine bag holding devices now present in the prior art, the present invention provides a new urine bag holder construction wherein the same can be utilized for removably holding a urine bag to a leg of a user.

The general purpose of the present invention, which will be described subsequently in greater detail, is to provide a new urine bag holder apparatus and method which has many of the advantages of the urine bag holding devices mentioned heretofore and many novel features that result in a new urine bag holder which is not anticipated, rendered obvious, suggested, or even implied by any of the prior art urine bag holding devices, either alone or in any combination thereof.

To attain this, the present invention generally comprises a panel having a top edge, a bottom edge, a first end edge and a second end edge. The panel comprising a flexible material having a inside surface and an outside surface. Each of a plurality of straps is attached to the outside surface and is positioned generally adjacent to the first end edge. Each of a plurality of fastening members removably fastens free ends of each of the straps to the outside surface of the panel. A plurality of securing members removably secure a urine bag to the panel by engaging holes in the urine bag.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new urine bag holder apparatus and method which has many of the advantages of the urine bag holding devices mentioned heretofore and many novel features that result in a new urine bag holder which is not anticipated, rendered obvious, suggested, or even implied by any of the prior art urine bag holding devices, either alone or in any combination thereof.

It is another object of the present invention to provide a new urine bag holder which may be easily and efficiently manufactured and marketed.

It is a further object of the present invention to provide a new urine bag holder which is of a durable and reliable construction.

An even further object of the present invention is to provide a new urine bag holder which is susceptible of a low cost of manufacture with regard to both materials and labor, and which accordingly is then susceptible of low prices of sale to the consuming public, thereby making such urine bag holder economically available to the buying public.

Still yet another object of the present invention is to provide a new urine bag holder which provides in the apparatuses and methods of the prior art some of the advantages thereof, while simultaneously overcoming some of the disadvantages normally associated therewith.

Still another object of the present invention is to provide a new urine bag holder for removably holding a urine bag to a leg of a user.

Yet another object of the present invention is to provide a new urine bag holder which includes a panel having a top edge, a bottom edge, a first end edge and a second end edge. The panel comprising a flexible material having a inside surface and an outside surface. Each of a plurality of straps is attached to the outside surface and is positioned generally adjacent to the first end edge. Each of a plurality of fastening members removably fastens free ends of each of the straps to the outside surface of the panel. A plurality of securing members removably secure a urine bag to the panel by engaging holes in the urine bag.

Still yet another object of the present invention is to provide a new urine bag holder that by incorporating numerous straps and the positioning of the straps allows for greater comfort to the user than previously found in the art.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
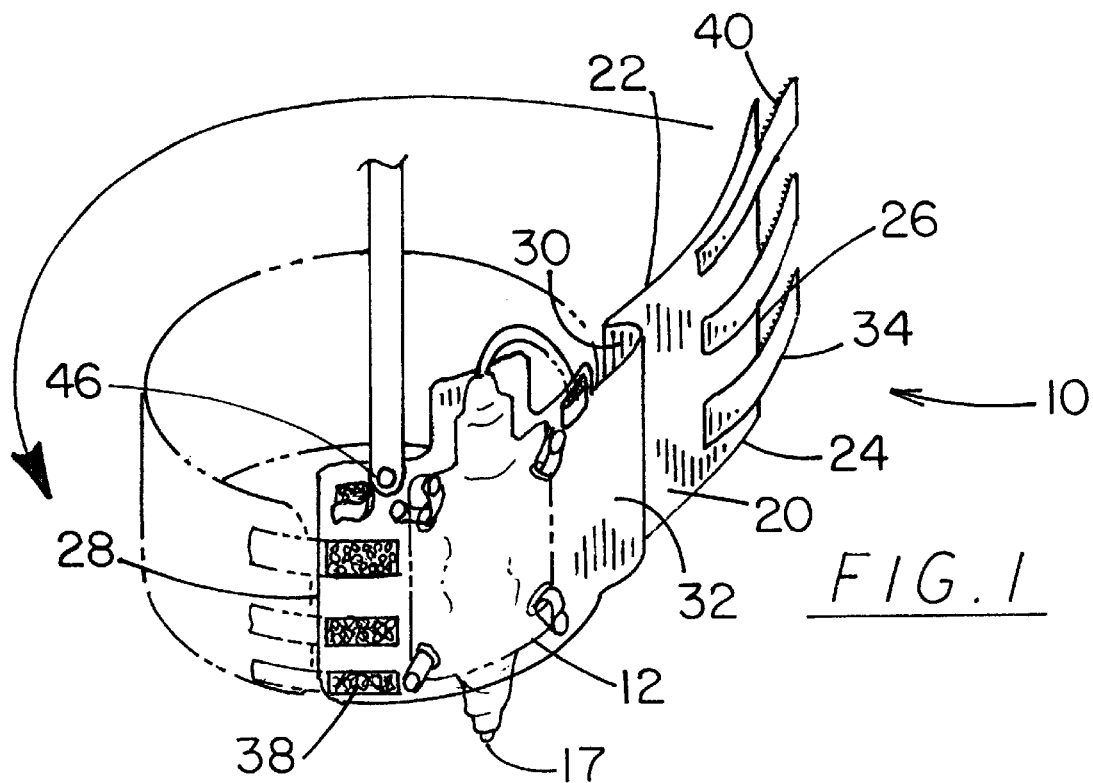
FIG. 1 is a schematic perspective view of a new urine bag holder according to the present invention.
Figure 2:
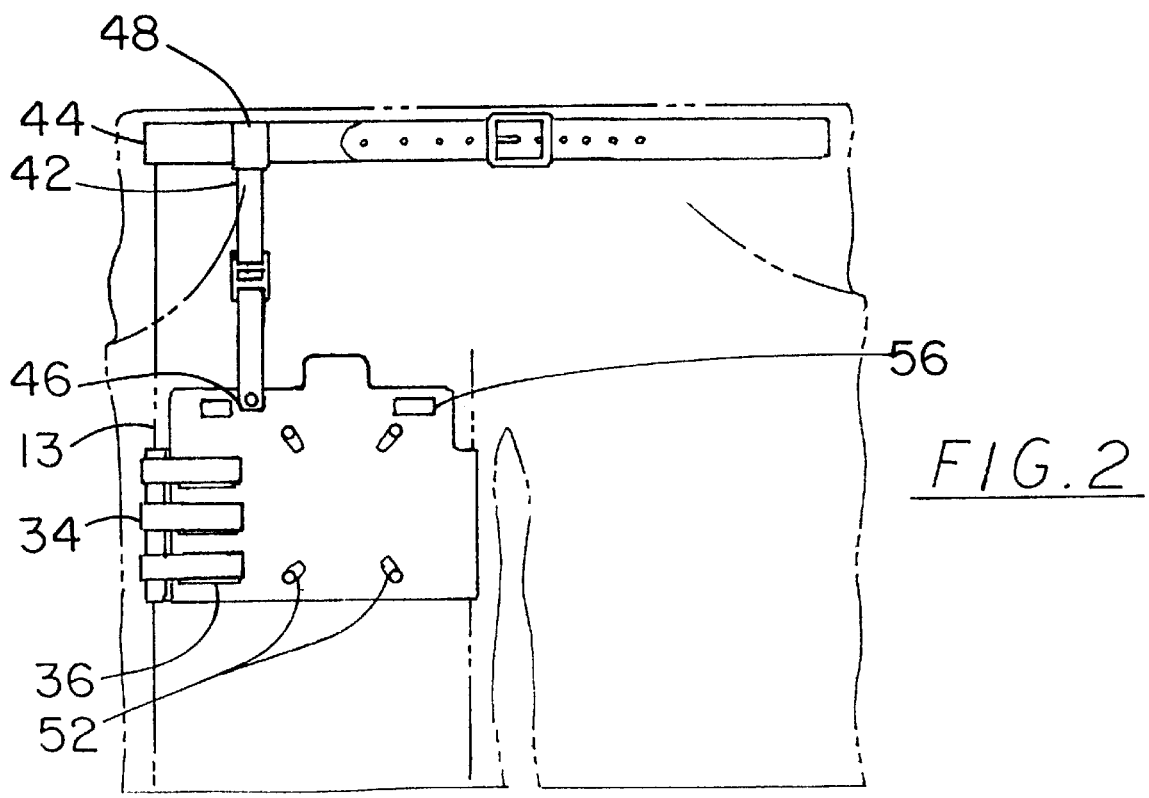
FIG. 2 is a schematic front view of the present invention.
Figure 3:
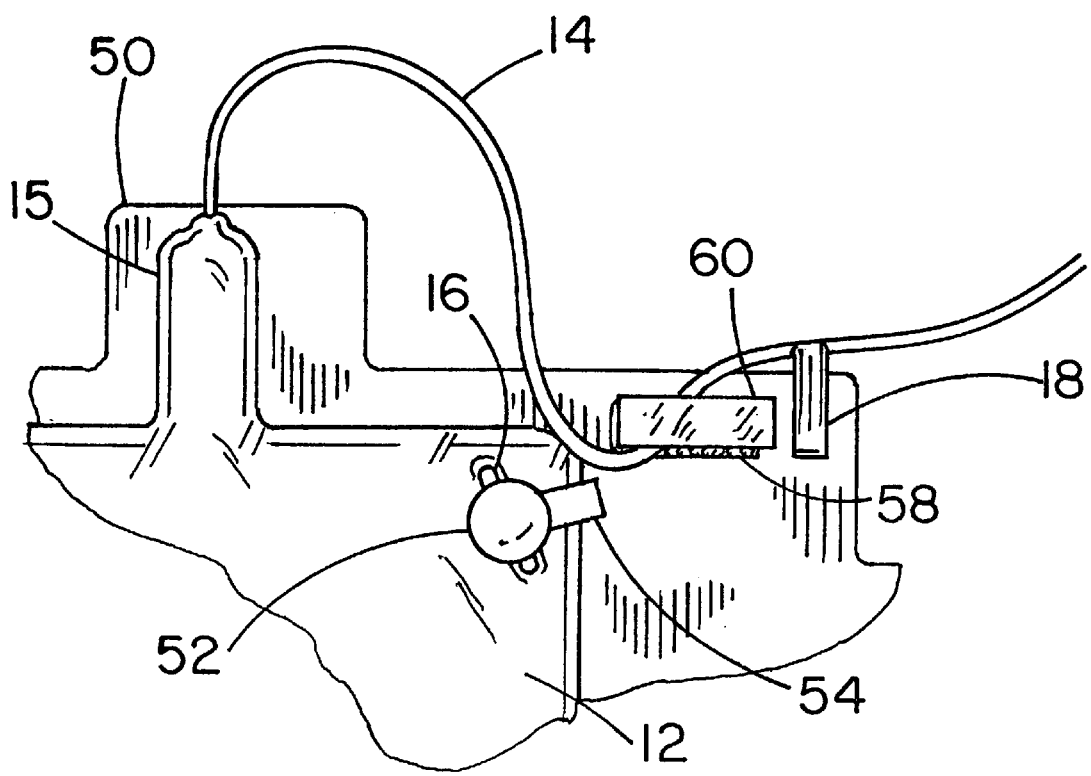
FIG. 3 is a schematic front view of the present invention.

With reference now to the drawings, and in particular to FIGS. 1 through 3 thereof, a new urine bag holder embodying the principles and concepts of the present invention and generally designated by the reference numeral 10 will be described.

As best illustrated in FIGS. 1 through 3, the urine bag holder 10 generally comprises a device for holding a urine bag 12 to the leg 13 of a user. The urine bag 12 has a tube 14 fluidly coupled thereto and extending upwardly from a neck 15 of the urine bag 12. The urine bag has four corners each having a hole 16 extending therethrough. The holes 16 in the urine bag do not compromise the integrity of a watertight nature of the urine bag but are used for coupling the urine bag to devices for holding the urine bag. The urine bag has a drain valve 17 positioned opposite of the neck 15.

The device 10 includes a panel 20 having a top edge 22, a bottom edge 24, a first end edge 26 and a second end edge 28. The panel 20 comprises a flexible material having an inside surface 30 and an outside surface 32. Each of a plurality of straps 34 is attached to the outside surface 32 and is positioned generally adjacent to the first end edge 26. Each of a plurality of fastening members 36 removably fastens free ends of each of the straps 34 to the outside surface 32 of the panel 20. Each of the fastening members 36 comprises a hook and loop fastening means having a plurality of hook portions 38 attached to the outside surface 32 of the panel 20 and located adjacent to the second side edge 28 and a plurality of loop portions 40 each attached to one of the straps 34. The panel 20 is extended around the leg 13 and the straps 34 allow for adjustment of the circumference of the panel 20 when positioned around a leg as shown in FIG. 2.

A belt support 42 removably couples the panel 12 to a belt 44 of a user. The belt support 42 includes an elongated member having a first end 46 attached to the outside surface 32 of the panel 20 and located adjacent to the top edge 22 of the panel 20. The elongated member 42 has a second end 48 defining a loop. The belt 44 of a user may be extended through the loop 48. The belt support 42 is positioned nearer the second side edge 28 than the first side edge 26 and prevents the panel 20 from moving down the leg 13 of a user while the user is in an upright position. The belt support 42 is ideally has an adjustable length for providing for different placement of the panel 20 with respect to the belt 44.

A flap 50 is attached to and extends upwardly from the top edge 22 of the panel 20. The flap 50 is located nearer the second side edge 28 than the first side edge 26. The neck 15 of the urine bag 12 is abuttable against the flap 50.

A plurality of securing members 52 removably secures the urine bag 12 to the panel 20. The securing members 52 are positioned nearer the second side edge 28 than the first side edge 26. Each of the securing members 52 is located such that each is extendable through one of the holes 16 in the urine bag 12 when the neck 15 is abutting the flap 50. Wherein, two of the securing members 52 are adjacent to the top edge 22 and spaced from each other and two are adjacent to the bottom edge 24 and spaced from each other. Each of the securing members 52 comprises a button coupled to the panel. The buttons 52 may be any type of conventional buttons including snaps coupled to relatively short ties 54.

A coupler holds 56 the tube is attached to the panel 20 and is located generally adjacent to the top edge 22. The coupler 56 is located between the flap 50 and the first side edge 26. The coupler 56 ideally includes a first pad 58 and a second pad 60. The first pad 58 is attached to the panel 20 adjacent to a securing member 52 and the second pad 60 is attached to the first pad 58 by a hook and loop fastening means. The tube 14 is placed on the first pad 58 and the second pad 60 is placed over the tube 14 and attached to the first pad 58 to hold the tube 14 between the first 58 and second 60 pads. The first panel 58 may have an end coupled to the second panel 60 such that the two remain together.

In use, the device 10 is adapted for the comfort and easy use by the wearer. The securing members 52 hold the urine bag 12 in such a manner that it is tight against the leg 13 and prevents the urine bag 12 from directly touching the leg of the wearer. The coupler 56 prevents the tube 14 from moving around and places the water-fill catheter 18 in a position for easy access and holds it against the panel 20 so that it 18 does not irritate the skin of the wearer. The straps 34 are positioned by the urine bag 12 so that they are easily positioned on the front portion of the leg. The belt 44 may be a conventional adjustable belt or a waistband formed from elastic to be positioned around the waist of a user. The positioning of the support belt adjacent to the second side edge 28 allows the urine bag 12 to be positioned between the legs 13 of the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A urine bag carrier device for holding a urine bag to the leg of a user, the urine bag having a tube fluidly coupled thereto and extending upwardly from a neck of the urine bag, the urine bag having four corners each having a hole extending therethrough, the holes in said urine bag not compromising the integrity of a watertight nature of the urine bag, said device comprising:

a panel having a top edge, a bottom edge, a first end edge and a second end edge, said panel comprising a flexible material having a inside surface and an outside surface, each of a plurality of straps being attached to said outside surface and being positioned generally adjacent to said first end edge, each of a plurality of fastening members removably fastening free ends of each of said straps to said outside surface of said panel, each of said fastening members comprising a hook and loop fastening means having a plurality of hook portions attached to said outside surface of said panel and located adjacent to said second side edge and a plurality of loop portions each attached to one of said straps;

a belt support for removably coupling said panel to a belt of a user, said belt support including an elongated member having a first end attached to said outside surface of said panel and located adjacent to said top edge of said panel, said elongated member having a second end defining a loop, wherein the belt of a user may be extended through said loop, said belt support being positioned nearer said second side edge than said first side edge;

a flap being attached to and extending upwardly from said top edge of said panel, said flap being located nearer said second side edge than said first side edge, wherein said neck of said urine bag is abuttable against said flap;

a plurality of securing members removably secure said urine bag to said panel, said securing members being positioned nearer said second side edge than said first side edge, each of said securing members being located such that each is extendable through one of said holes in said urine bag when said neck is abutting said flap, each of said securing members comprising a button coupled to said panel; and a coupler for holding said tube being attached to said panel and located generally adjacent to said top edge, said coupler being located between said flap and said first side edge, said coupler having a first pad attached to said panel and a second pad, said second pad is attached to said first pad, said second pad being positionable over said tube, said second pad having a second end selectively couplable to said first pad such that said tube is held between said first and second pads.

* * * * *